US008962515B2

(12) United States Patent
Nagaki et al.

(10) Patent No.: US 8,962,515 B2
(45) Date of Patent: Feb. 24, 2015

(54) CATALYST FOR PRODUCING ACRYLIC ACIDS AND ACRYLATES

(71) Applicant: Celanese International Corporation, Irving, TX (US)

(72) Inventors: Dick Nagaki, The Woodlands, TX (US); Craig J. Peterson, Houston, TX (US); Heiko Weiner, Pasadena, TX (US); Elizabeth Bowden, Houston, TX (US); Josefina T. Chapman, Houston, TX (US); Sean Mueller, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 147 days.

(21) Appl. No.: 13/664,478

(22) Filed: Oct. 31, 2012

(65) Prior Publication Data

US 2013/0245308 A1    Sep. 19, 2013

Related U.S. Application Data

(60) Provisional application No. 61/610,108, filed on Mar. 13, 2012.

(51) Int. Cl.
| | | |
|---|---|---|
| *B01J 27/198* | (2006.01) | |
| *C07C 51/00* | (2006.01) | |
| *C07C 67/30* | (2006.01) | |
| *C07B 35/00* | (2006.01) | |

(52) U.S. Cl.
USPC .......................... 502/209; 560/211; 562/599

(58) Field of Classification Search
USPC ................... 502/209; 560/211; 562/299, 599
See application file for complete search history.

(56) References Cited

U.S. PATENT DOCUMENTS

| | | | |
|---|---|---|---|
| 3,135,783 | A | 6/1964 | Sennewald et al. |
| 4,132,670 | A | 1/1979 | Katsumoto et al. |
| 4,165,438 | A | 8/1979 | Schneider |
| 4,178,304 | A | 12/1979 | Litvishkov et al. |
| 4,263,181 | A * | 4/1981 | Wagner et al. .................. 524/14 |
| 4,444,741 | A * | 4/1984 | Hass et al. .................... 423/542 |
| 4,892,856 | A | 1/1990 | Kawajiri et al. |
| 4,994,608 | A | 2/1991 | Torrence et al. |
| 5,144,068 | A | 9/1992 | Smith et al. |
| 5,364,824 | A | 11/1994 | Andrews et al. |
| RE35,377 | E | 11/1996 | Steinberg et al. |
| 5,599,976 | A | 2/1997 | Scates et al. |
| 5,821,111 | A | 10/1998 | Grady et al. |
| 6,143,930 | A | 11/2000 | Singh et al. |
| 6,232,352 | B1 | 5/2001 | Vidalin et al. |
| 6,509,180 | B1 | 1/2003 | Verser et al. |
| 6,544,924 | B1 | 4/2003 | Jackson et al. |
| 6,627,770 | B1 | 9/2003 | Cheung et al. |
| 6,657,078 | B2 | 12/2003 | Scates et al. |
| 6,685,754 | B2 | 2/2004 | Kindig et al. |
| 6,927,048 | B2 | 8/2005 | Verser et al. |
| 7,005,541 | B2 | 2/2006 | Cheung et al. |
| 7,053,147 | B2 | 5/2006 | Jackson et al. |
| 7,074,603 | B2 | 7/2006 | Verser et al. |
| 7,115,772 | B2 | 10/2006 | Picard et al. |
| 7,208,624 | B2 | 4/2007 | Scates et al. |
| 7,351,559 | B2 | 4/2008 | Verser et al. |
| 7,507,562 | B2 | 3/2009 | Verser et al. |
| 7,601,865 | B2 | 10/2009 | Verser et al. |
| 7,682,812 | B2 | 3/2010 | Verser et al. |
| 7,851,397 | B2 | 12/2010 | Liang et al. |
| 7,884,253 | B2 | 2/2011 | Stites et al. |
| 7,888,082 | B2 | 2/2011 | Verser et al. |
| 8,143,444 | B2 | 3/2012 | Mariansky et al. |
| 8,642,498 | B2 * | 2/2014 | Nagaki et al. .................. 502/206 |
| 8,652,988 | B2 * | 2/2014 | Nagaki et al. .................. 502/209 |
| 8,735,314 | B2 * | 5/2014 | Nagaki et al. .................. 502/150 |
| 2005/0261522 | A1 | 11/2005 | Isaguliants et al. |
| 2007/0021630 | A1 | 1/2007 | Liang et al. |
| 2008/0193989 | A1 | 8/2008 | Verser et al. |
| 2009/0281354 | A1 | 11/2009 | Mariansky et al. |
| 2011/0071311 | A1 | 3/2011 | Johnson et al. |
| 2012/0071687 | A1 | 3/2012 | Herzog et al. |
| 2012/0071688 | A1 | 3/2012 | Herzog et al. |
| 2013/0053599 | A1* | 2/2013 | Weiner et al. .................. 560/211 |
| 2013/0245310 | A1* | 9/2013 | Nagaki et al. .................. 560/210 |
| 2014/0135527 | A1* | 5/2014 | Nagaki et al. .................. 562/599 |

FOREIGN PATENT DOCUMENTS

| | | | |
|---|---|---|---|
| EP | 1967507 | 9/2008 | |
| GB | 969369 | 9/1964 | |
| WO | 2013/137934 | * 9/2013 | ............ C07C 67/343 |
| WO | 2014/070735 | * 5/2014 | ............ C07C 67/343 |

OTHER PUBLICATIONS

Monros, et al., Journal of Material Science, vol. 28, p. 5832 (1993).
Jubb & Bowen, Journal of Material Science, vol. 22, pp. 1963-1970 (1987).
International Search Report and Written Opinion mailed Apr. 17, 2013 in corresponding International Application No. PCT/US2012/062710.
Iler R K, The Chemistry of Silica, (Wiley, New York, 1979).
Brinker C J & Scherer G W, "Sol-Gel Science" published by Academic Press (1990).
Bosman, et al., Journal of Catalysis, vol. 148, p. 660 (1994).
M. Ai., Shokubai, 29, 522 (1987).
M. Ai., J. Catal., 124, 293 (1990).
M. Ai., J. Catal., 107, 201 (1987).
M. Ai., Appl. Catal., 36, 221 (1988).

* cited by examiner

*Primary Examiner* — Patricia L Hailey

(57) ABSTRACT

In one embodiment, the invention is to a process for producing an acrylate product. The process includes the steps of contacting an alkanoic acid and an alkylenating agent over a catalyst composition under conditions effective to produce the acrylate product. The catalyst composition comprises a metal phosphate matrix containing vanadium and bismuth. Preferably, the catalyst comprises, in an active phase, vanadium to bismuth at a molar ratio of at least 0.02:1. Preferably, the catalyst composition is substantially free of titanium.

22 Claims, No Drawings

CATALYST FOR PRODUCING ACRYLIC ACIDS AND ACRYLATES

CROSS REFERENCE TO RELATED APPLICATION

This application claims priority to U.S. Provisional Application No. 61/610,108, filed on Mar. 13, 2012, the entire contents and disclosures of which are incorporated herein by reference.

FIELD OF THE INVENTION

The present invention relates generally to the production of acrylic acid. More specifically, the present invention relates to a catalyst for use in the production of acrylic acid via the aldol condensation of acetic acid and formaldehyde.

BACKGROUND OF THE INVENTION $\alpha,\beta$-unsaturated acids, particularly acrylic acid and methacrylic acid, and the ester derivatives thereof are useful organic compounds in the chemical industry. These acids and esters are known to readily polymerize or co-polymerize to form homopolymers or copolymers. Often the polymerized acids are useful in applications such as superabsorbents, dispersants, flocculants, and thickeners. The polymerized ester derivatives are used in coatings (including latex paints), textiles, adhesives, plastics, fibers, and synthetic resins.

Because acrylic acid and its esters have long been valued commercially, many methods of production have been developed. One exemplary acrylic acid ester production process involves the reaction of acetylene with water and carbon monoxide. Another conventional process involves the reaction of ketene (often obtained by the pyrolysis of acetone or acetic acid) with formaldehyde. These processes have become obsolete for economic, environmental, or other reasons.

Another acrylic acid production method utilizes the condensation of formaldehyde and acetic acid and/or carboxylic acid esters. This reaction is often conducted over a catalyst. For example, condensation catalyst consisting of mixed oxides of vanadium, titanium, and/or phosphorus were investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, *Shokubai*, 29, 522 (1987). These catalysts have a vanadium:titanium:phosphorus molar ratio of 1:2:x, where x is varied from 4.0 to 7.0, and have traditionally shown that the catalyst activity decreases steadily condensation products, e.g., acrylic acid and methyl acrylate, was obtained where x was 6.0. With these catalysts, the molar ratio of vanadium to titanium was maintained at or below 1:2. The acetic acid conversions achieved using these catalysts, however, leave room for improvement.

Even in view of these references, the need exists for improved processes for producing acrylic acid, and for an improved catalyst capable of providing high acetic acid conversions and acrylate product yields.

SUMMARY OF THE INVENTION

In one embodiment, the present invention relates to a catalyst composition suitable for use in an aldol condensation of an alkanoic acid and an alkylenating agent to form an acrylate product. The catalyst composition comprises an active phase comprising vanadium and bismuth. Preferably, the acrylate product has a yield of greater than 30%. Preferably, these components are present in the active phase of the catalyst composition in a molar ratio of vanadium to bismuth of at least 0.02:1. Preferably, the catalyst composition is free of titanium.

In another embodiment, the present invention relates to a process for producing an acrylate product, the process comprising the steps of: (a) contacting an alkanoic acid and an alkylenating agent over a catalyst, e.g., the above-identified catalyst, under conditions effective to produce the acrylate product, (b) wherein the catalyst comprises vanadium and bismuth. Preferably, the alkylenating agent is formaldehyde, the alkanoic acid is acetic acid, and the acrylate product is acrylic acid. In one embodiment, the overall alkanoic acid conversion in the reaction is at least 20 mol % and the space time yield of acrylate product is at least 40 grams/hr/L of catalyst.

In another embodiment, the invention is to a process for producing the above-identified catalyst. The process comprises the steps of: (a) contacting a vanadium precursor and a bismuth precursor to form a wet catalyst precursor mixture, and (b) calcining the wet catalyst precursor mixture to form a dried catalyst composition comprising vanadium and bismuth. The process may further comprise the step of mixing a vanadium precursor and a reductant solution to form a vanadium precursor solution. The contacting step may comprise the step of contacting a binder with the bismuth precursor, and/or the vanadium precursor solution to form the wet catalyst precursor mixture.

DETAILED DESCRIPTION OF THE INVENTION

Introduction

Production of unsaturated carboxylic acids such as acrylic acid and methacrylic acid and the ester derivatives thereof via most conventional processes have been limited by economic and environmental constraints. One of the more practical processes for producing these acids and esters involves the aldol condensation of formaldehyde and (i) acetic acid and/or (ii) ethyl acetate over a catalyst. Exemplary classes of conventional catalyst include vanadium-silica-phosphates, and alkali metal-promoted silicas, e.g., cesium- or potassium-promoted silicas. The alkali metal-promoted silicas, however, have been known to exhibit only low to moderate activity when used in aldol condensation reactions.

Heteropolyacid catalysts comprising bismuth have also been studied. U.S. Pat. No. 7,851,397 teaches the use of a heteropolyacid catalyst for oxidizing unsaturated and/or saturated aldehydes, such as acrolein or methacrolein, to unsaturated acids, such as acrylic acid or methacrylic acid. The catalyst contains molybdenum, phosphorus, vanadium, bismuth and a first component selected from the group consisting of potassium, rubidium, cesium, thallium and a mixture thereof. The methods for making these heteropolyacid catalysts are cumbersome as they involve the addition of each metal solution individually to an ammonium paramolybdate solution.

It has now been discovered that certain catalysts effectively catalyze the aldol condensation of a carboxylic acid with an alkylenating agent, e.g. a methylenating agent, such as formaldehyde to form an unsaturated acid. Preferably, the reaction is an aldol condensation reaction of acetic acid with formaldehyde to form acrylate product(s), e.g., acrylic acid.

In one embodiment, the present invention is to a process for producing acrylic acid, methacrylic acid, and/or the salts and esters thereof. As used herein, acrylic acid, methacrylic acid, and/or the salts and esters thereof, collectively or individually, may be referred to as "acrylate product" or "acrylate products." The use of the terms acrylic acid, methacrylic acid, or the salts and esters thereof, individually, does not exclude the other acrylate products, and the use of the term acrylate product does not require the presence of acrylic acid, methacrylic acid, and the salts and esters thereof.

Accordingly, in one embodiment, the present invention relates to a catalyst composition suitable for use in an aldol condensation of acetic acid and formaldehyde. The catalyst composition comprises vanadium and bismuth. In one embodiment, the catalyst composition comprises a metal phosphate matrix and the matrix contains vanadium and bismuth. The catalyst composition may be substantially free of titanium. Surprisingly and unexpectedly, the vanadium-bismuth catalyst provides high conversions, selectivities, and yields when employed in the aldol condensation reaction, as compared to conventional aldol condensation catalysts, which do not utilize the vanadium-bismuth combination.

The inventive catalyst composition has a low deactivation rate and provides stable performance over time, e.g., over 0.8 hours, over 3 hours, over 5 hours, over 10 hours, over 25 hours, over 60 hours, or over 100 hours, when utilized in the aldol condensation reaction.

In one embodiment, vanadium and bismuth are present as respective oxides or phosphates or mixtures thereof. The catalyst composition may comprise an active phase, which comprises the components that promote the catalysis, and may also comprise a support or a modified support. As one example, the active phase comprises metals, phosphorus-containing compounds, and oxygen-containing compounds. In a preferred embodiment, vanadium and bismuth are present in the active phase. Preferably, the molar ratio of vanadium to bismuth in the active phase of the catalyst composition is at least 0.02:1, e.g., at least 0.1:1, at least 0.25:1, at least 0.5:1, or at least 2:1. In terms of ranges, the molar ratio of vanadium to bismuth in the inventive catalyst may range from 0.02:1 to 1000:1, e.g., from 0.1:1 to 10:1, from 0.25:1 to 4:1, or from 0.5:1 to 2:1.

In one embodiment, the catalyst composition is substantially free of titanium, e.g., in the active phase, e.g. the catalyst composition comprises less than 5.0 wt % titanium, e.g., less than 1.0 wt %, or less than 0.1 wt %.

The inventive catalyst has been found to achieve unexpectedly high acetic acid conversions. For example, depending on the temperature at which the acrylate product, e.g., acrylic acid, formation reaction is conducted, alkanoic acid conversions of at least 20 mol %, e.g., at least 30 mol %, at least 40 mol %, or at least 50 mol %, may be achieved with this catalyst composition. This increase in acetic acid conversion is achieved while maintaining high selectivity to the desired acrylate product such as acrylic acid or methyl acrylate. For example, selectivities to the desired acrylate product of at least 35 mol %, e.g., at least 45 mol %, at least 60 mol %, at least 70 mol %, or at least 75 mol %, may be achieved with the catalyst composition of the present invention. Acrylate product yield is calculated by multiplying alkanoic acid conversion and acrylate product selectivity. Acrylate product yield may be greater than 7%, greater than 13.5%, greater than 24%, greater than 30%, or greater than 35%.

The total amounts of vanadium and bismuth in the catalyst composition of the invention may vary widely. In some embodiments, for example, the catalyst composition comprises in the active phase at least 0.3 wt % vanadium, e.g., at least 1.5 wt %, at least 3.5 wt %, at least 6 wt % or at least 10 wt %, based on the total weight of the active phase of the catalyst composition. The catalyst composition may comprise in the active phase at least 0.1 wt % bismuth, e.g., at least 10 wt %, at least 20 wt %, at least 30 wt % or at least 45 wt % bismuth. In terms of ranges, the catalyst composition may comprise in the active phase from 0.3 to 40 wt % vanadium, e.g., from 0.3 to 35 wt %, from 0.3 wt % to 32.5 wt %, from 1.0 wt % to 32 wt % or from 5 wt % to 20 wt %; and/or 0.1 wt % to 75 wt % bismuth, e.g., from 11 wt % to 70 wt % or from 20 wt % to 65 wt %, from 30 wt % to 60 wt %, from 0.1 to 10 wt %, from 0.3 to 5 wt %, or from 0.5 to 3 wt %. The catalyst composition may comprise in the active phase at most 32 wt % vanadium, e.g., at most 28 wt %, e.g., at most 23 wt % or at most 18 wt %. The catalyst composition may comprise in the active phase at most 75 wt % bismuth, e.g., at most 68 wt %, e.g., at most 64 wt %, at most 58 wt % or at most 50 wt %. In one embodiment, the catalyst comprises in the active phase vanadium and bismuth, in combination, in an amount greater than 25 wt %, e.g., greater than 35 wt %, greater than 40 wt %, greater than 50 wt %, or greater than 55 wt %. In terms of ranges, the combined weight percentage of the vanadium and bismuth, in combination in the active phase may range from 25 wt % to 75 wt %, e.g., from 35 wt % to 70 wt %, from 42 wt % to 68 wt %, or from 47 wt % to 64 wt %.

In other embodiments, the inventive catalyst may further comprise other compounds or elements (metals and/or non-metals). For example, the catalyst may further comprise phosphorus and/or oxygen. In these cases, the catalyst may comprise in the active phase from 7 wt % to 25 wt % phosphorus, e.g., from 10 wt % to 21 wt %, from 10 wt % to 21 wt %, or from 11 wt % to 19 wt %; and/or from 15 wt % to 55 wt % oxygen, e.g., from 18 wt % to 45 wt %, or from 25 wt % to 36 wt %.

In some embodiments, the bismuth is present in the form of a bismuth salt, including bismuth (III) and (V) salts. For example, the catalyst composition may comprise the bismuth salt in an amount ranging from 0.1 wt % to 75 wt %, e.g., from 11 wt % to 70 wt %, from 20 wt % to 65 wt %, or from 30 wt % to 60 wt %. Preferably the bismuth salt used in the preparation of the inventive catalyst is a bismuth (III) salt. The bismuth salt may for instance be selected from bismuth carboxylates, bismuth halides, bismuth acetate, bismuth sulphadiazine, bismuth sulphate, bismuth nitrate, bismuth subnitrate, bismuth carbonate, bismuth subcarbonate, bismuth oxide, bismuth oxychloride, bismuth hydroxide, bismuth phosphate, bismuth aluminate, bismuth tribromophenate, bismuth thiol, bismuth peptides, bismuth salts of quinolines and their derivatives, e.g., bismuth hydroxyquinolines, bismuth pyrithione and other bismuth salts of pyridine thiols, bismuth amino acid salts such as the glycinate, tripotassium dicitrato bismuthate, and mixtures thereof. In some embodiments, acid solutions such as nitric acid or acetic acid may be used to dissolve the bismuth salt to form a bismuth solution.

Generally speaking the bismuth salt may be either organic or inorganic. It may be a basic bismuth salt (bismuth subsalt) such as the subsalts referred to above.

Suitable bismuth carboxylates include the salicylate, subsalicylate, lactate, citrate, subcitrate, ascorbate, acetate, dipropylacetate, tartrate, sodium tartrate, gluconate, subgallate, benzoate, laurate, myristate, palmitate, propionate, stearate, undecylenate, aspirinate, neodecanoate and ricinoleate. Of these, basic bismuth salicylate (bismuth subsalicylate) and bismuth citrate may be preferred. Suitable halides include bismuth chloride, bismuth bromide and bismuth iodide. Preferred bismuth salts may be selected from bismuth halides, bismuth nitrates, bismuth acetate, and bismuth carboxylates, such as bismuth subsalicylate, bismuth salicylate, bismuth subgallate, bismuth subcitrate, bismuth citrate, bismuth nitrate and bismuth subnitrate.

In one embodiment, the formation of the catalyst composition may utilize the reduction of a pentavalent vanadium compound. The reduced pentavalent compound may be combined with a phosphorus compound and, optionally, promoters under conditions effective to provide or maintain the vanadium in a valence state below +5 to form the active metal phosphate catalysts. Various reducing agents and solvents may be used to prepare these catalysts. Examples include organic acids, alcohols, polyols, aldehydes, and hydrochloric acid. Generally speaking, the choice of the metal precursors, reducing agents, solvents, sequence of addition, reaction conditions such as temperature and times, and calcination temperatures may impact the catalyst composition, surface area, porosity, structural strength, and overall catalyst performance.

In one embodiment, suitable vanadium compounds that serve as a source of vanadium in the catalyst composition contain pentavalent vanadium and include, but are not limited to, vanadium pentoxide or vanadium salts such as ammonium metavanadate, vanadium oxytrihalides, vanadium alkylcarboxylates and mixtures thereof.

In one embodiment, suitable phosphorus compounds that serve as a source of phosphorus in the catalyst contain pentavalent phosphorus and include, but are not limited to, phosphoric acid, phosphorus pentoxide, polyphosphoric acid, or phosphorus perhalides such as phosphorus pentachloride, and mixtures thereof.

In one embodiment, the active phase of the catalyst corresponds to the formula:

$$V_a Bi_b P_c O_d,$$

wherein:
a is 1 to 100,
b is from 0.1 to 50,
c is from 1 to 165, and
d is from 4 to 670.

The letters a, b, c, and d are the relative molar amounts (relative to 1.0) of vanadium, bismuth, phosphorus and oxygen, respectively in the catalyst. In these embodiments, the ratio of a to b is greater than 0.02:1, e.g., greater than 5:1, greater than 10:1, or greater than 20:1. Preferred ranges for molar variables a, b, c, and d are shown in Table 1.

TABLE 1

|   | Molar Range | Molar Range | Molar Range |
|---|---|---|---|
| a | 1 to 100 | 1 to 10 | 1 to 4 |
| b | 0.1 to 50 | 0.5 to 10 | 1 to 4 |
| c | 1 to 165 | 1 to 16 | 1 to 7 |
| d | 4 to 670 | 5 to 60 | 5 to 25 |

In some embodiments, the catalyst composition further comprises additional metals and/or metal oxides. These additional metals and/or metal oxides may function as promoters. If present, the additional metals and/or metal oxides may be selected from the group consisting of copper, molybdenum, nickel, niobium, and combinations thereof. Other exemplary promoters that may be included in the catalyst of the invention include lithium, sodium, magnesium, aluminum, chromium, manganese, iron, cobalt, calcium, yttrium, ruthenium, silver, tin, barium, lanthanum, the rare earth metals, hafnium, tantalum, rhenium, thorium, bismuth, antimony, germanium, zirconium, uranium, cesium, zinc, and silicon and mixtures thereof. Other modifiers include boron, gallium, arsenic, sulfur, halides, Lewis acids such as $BF_3$, $ZnBr_2$, and $SnCl_4$. Exemplary processes for incorporating promoters into catalyst are described in U.S. Pat. No. 5,364,824, the entirety of which is incorporated herein by reference.

If the catalyst composition comprises additional metal(s) and/or metal oxides(s), the catalyst optionally may comprise additional metals and/or metal oxides in an amount from 0.001 wt % to 30 wt %, e.g., from 0.01 wt % to 5 wt % or from 0.1 wt % to 5 wt %. If present, the promoters may enable the catalyst to have a weight/weight space time yield of at least 25 grams of acrylic acid/gram catalyst-h, e.g., at least 50 grams of acrylic acid/gram catalyst-h, or at least 100 grams of acrylic acid/gram catalyst-h.

In some embodiments, the catalyst composition is unsupported. In these cases, the catalyst may comprise a homogeneous mixture or a heterogeneous mixture as described above.

In one embodiment, the homogeneous mixture is the product of an intimate mixture of vanadium and bismuth resulting from preparative methods such as controlled hydrolysis of metal alkoxides or metal complexes. In other embodiments, the heterogeneous mixture is the product of a physical mixture of the vanadium and bismuth salt. These mixtures may include formulations prepared from phosphorylating a physical mixture of preformed hydrous metal oxides. In other cases, the mixture(s) may include a mixture of preformed vanadium pyrophosphate powder.

In another embodiment, the catalyst composition is a supported catalyst comprising a catalyst support in addition to the vanadium and bismuth and optionally phosphorous and oxygen, in the amounts indicated above (wherein the molar ranges indicated are without regard to the moles of catalyst support, including any vanadium, bismuth, phosphorous or oxygen contained in the catalyst support). The total weight of the support (or modified support), based on the total weight of the catalyst, preferably is from 25 wt % to 95 wt %, e.g., from 40 wt % to 70 wt % or from 50 wt % to 60 wt %, and the total weight of the active phase is from 0.1 wt % to 25 wt %, based on the total weight of the catalyst composition. In a preferred embodiment, the weight of the active phase is at least 6 wt % of the total catalyst composition weight.

The support may vary widely. In one embodiment, the support material is selected from the group consisting of silica, alumina, zirconia, titania, aluminosilicates, zeolitic materials, mixed metal oxides (including but not limited to binary oxides such as $SiO_2$—$Al_2O_3$, $SiO_2$—$TiO_2$, $SiO_2$—$ZnO$, $SiO_2$—$MgO$, $SiO_2$—$ZrO_2$, $Al_2O_3$—$MgO$, $Al_2O_3$—$TiO_2$, $Al_2O_3$—$ZnO$, $TiO_2$—$MgO$, $TiO_2$—$ZrO_2$, $TiO_2$—$ZnO$, $TiO_2$—$SnO_2$) and mixtures thereof, with silica being one preferred support. Other suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, silicon carbide, sheet silicates or clay minerals such as montmorillonite, beidellite, saponite, pillared clays, and mixtures thereof. Other supports may include, but are not limited to, iron oxide, magnesia, steatite, magnesium oxide, carbon, graphite, high surface area graphitized carbon, activated carbons, and mixtures thereof. Other supports may include coated structured forms such as coated metal foil, sintered metal forms and coated ceramic formed shapes such as shaped cordierite, platy alumina or acicular mullite forms. These listings of supports are merely exemplary and are not meant to limit the scope of the present invention.

In other embodiments, in addition to the active phase and a support, the inventive catalyst may further comprise a support modifier. A modified support, in one embodiment, relates to a support that includes a support material and a support modifier, which, for example, may adjust the chemical or physical properties of the support material such as the acidity or basicity of the support material. In embodiments that use a modified support, the support modifier is present in an amount from 0.1 wt % to 50 wt %, e.g., from 0.2 wt % to 25 wt %, from 0.5 wt % to 15 wt %, or from 1 wt % to 8 wt %, based on the total weight of the catalyst composition.

In one embodiment, the support modifier is an acidic support modifier. In some embodiments, the catalyst support is modified with an acidic support modifier. The support modifier similarly may be an acidic modifier that has a low volatility or little volatility. The acidic modifiers may be selected from the group consisting of oxides of Group IVB metals, oxides of Group VB metals, oxides of Group VIB metals, iron oxides, aluminum oxides, and mixtures thereof. In one embodiment, the acidic modifier may be selected from the group consisting of $WO_3$, $MoO_3$, $Fe_2O_3$, $Cr_2O_3$, $V_2O_5$, $MnO_2$, $CuO$, $Co_2O_3$, $Bi_2O_3$, $TiO_2$, $ZrO_2$, $Nb_2O_5$, $Ta_2O_5$, $Al_2O_3$, $B_2O_3$, $P_2O_5$, and $Sb_2O_3$.

In another embodiment, the support modifier is a basic support modifier. The presence of chemical species such as alkali and alkaline earth metals, are normally considered basic and may conventionally be considered detrimental to catalyst performance. The presence of these species, however, surprisingly and unexpectedly, may be beneficial to the catalyst performance. In some embodiments, these species may act as catalyst promoters or a necessary part of the acidic catalyst structure such in layered or sheet silicates such as montmorillonite. Without being bound by theory, it is postulated that these cations create a strong dipole with species that create acidity.

Additional modifiers that may be included in the catalyst include, for example, boron, aluminum, magnesium, zirconium, and hafnium.

In some embodiments in which a support is employed, the support may have a surface area of at least 1 $m^2/g$, e.g., at least 5 $m^2/g$ or at least 10 $m^2/g$, as determined by BET measurements. The catalyst support may include pores, optionally having an average pore diameter ranging from 5 nm to 200 nm, e.g., from 5 nm to 50 nm or from 10 nm to 25 nm. The catalyst optionally has an average pore volume of from 0.01 $cm^3/g$ to 3 $cm^3/g$, e.g., from 0.02 $cm^3/g$ to 0.1 $cm^3/g$ or from 0.02 $cm^3/g$ to 0.05 $cm^3/g$, as determined by BET measurements. Preferably, at least 50% of the pore volume or surface area, e.g., at least 70% or at least 80%, is provided by pores having the diameters discussed above. Pores may be formed and/or modified by pore modification agents, which are discussed below. In another embodiment, the ratio of microporosity to macroporosity ranges from 95:5 to 85:15, e.g., from 75:25 to 70:30. Microporosity refers to pores smaller than 2 nm in diameter, and movement in micropores may be described by activated diffusion. Mesoporosity refers to pores greater than 2 nm and less than 50 nm is diameter. Flow through mesopores may be described by Knudson diffusion. Macroporosity refers to pores greater than 50 nm in diameter and flow though macropores may be described by bulk diffusion. Thus, in some embodiments, it is desirable to balance the surface area, pore size distribution, catalyst or support particle size and shape, and rates of reaction with the rate of diffusion of the reactant and products in and out of the pores to optimize catalytic performance.

As will be appreciated by those of ordinary skill in the art, the support materials, if included in the catalyst of the present invention, preferably are selected such that the catalyst system is suitably active, selective and robust under the process conditions employed for the formation of the desired product, e.g., acrylic acid or alkyl acrylate. Also, the active metals that are included in the catalyst of the invention may be dispersed throughout the support, coated on the outer surface of the support (egg shell) or decorated on the surface of the support. In some embodiments, in the case of macro- and meso-porous materials, the active sites may be anchored or applied to the surfaces of the pores that are distributed throughout the particle and hence are surface sites available to the reactants but are distributed throughout the support particle.

The inventive catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include stearic acid, graphite, starch, methyl cellulose, silica, alumina, glass fibers, silicon carbide, and silicon nitride. In one embodiment, the active phase of the catalyst (not the support) comprises the other additives. For example, the active phase may comprise silica, e.g., colloidal silica. In such embodiments, the silica may be present in the active phase in amounts ranging from 0.01 to 50 wt % silica, e.g., from 0.1 to 40 wt %, from 0.5 wt % to 30 wt %, from 1.0 wt % to 30 wt %, or from 1 wt % to 20 wt %. In terms of lower limits, the active phase may comprise at least 0.01 wt % silica, e.g., at least 0.1 wt %, at least 0.5 wt %, or at least 1 wt %. In terms of upper limits, the active phase may comprise less than 50 wt % silica, e.g., less than 40 wt %, less than 30 wt %, or less than 20 wt %. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

In one embodiment, the inventive catalyst composition comprises a pore modification agent. In some embodiments, the pore modification agent may be thermally stable and has a substantial vapor pressure at a temperature below 300° C., e.g., below 250° C. In one embodiment, the pore modification agent has a vapor pressure of at least 0.1 kPa, e.g., at least 0.5 kPa, at a temperature between about 150° C. and about 250° C., e.g., between about 150° C. and about 200° C. In other embodiments, pore modification agent may be thermally decomposed or burned out to create pores. For example, the burned out agent may be cellulose-derived materials such as ground nut shells.

In some embodiments, the pore modification agent has a relatively high melting point, e.g., greater than 60° C., e.g., greater than 75° C., so that it does not melt during compression of the catalyst precursor into a slug, tablet, or pellet. Preferably, the pore modification agent comprises a relatively pure material rather than a mixture. As such, lower melting components will not liquefy under compression during formation of slugs or tablets. For example, where the pore modification agent is a fatty acid, lower melting components of the fatty acid mixtures may be removed as liquids by pressing. If this phenomenon occurs during slug or tablet compression, the flow of liquid may disturb the pore structure and produce an undesirable distribution of pore volume as a function of pore diameter on the catalyst composition. In other embodiments, the pore modification agents have a significant vapor pressure at temperatures below their melting points, so that they can be removed by sublimination into a carrier gas.

For example, the pore modification agent may be a fatty acid corresponding to the formula $CH_3(CH_2)_xCOOH$ where x>8. Exemplary fatty acids include stearic acid (x=16), palmitic acid (x=14), lauric acid (x=10), myristic acid (x=12). The esters of these acids and amides or other functionalized forms of such acids, for example, stearamide ($CH_3(CH_2)_{16}CONH_2$) may also be used. Suitable esters may include methyl esters as well as glycerides such as stearin (glycerol tristearate). Mixtures of fatty acids may be used, but substantially pure acids, particularly stearic acid, are generally preferred over mixtures.

In addition, while fatty acids and fatty acid derivatives are generally preferred, other compositions which meet the functional requirements discussed above are also suitable for use as pore modification agents. Other preferred pore modification agents include but are not limited to polynuclear organic compounds such as naphthalene, graphite, natural burnout components such as cellulose and its cellulosic derivatives, cellulose-derived materials, such as starches and ground nut shells, natural and synthetic oligomers and polymers such as polyethylene, polyvinyl alcohols and polyacrylic acids and esters.

Catalyst Preparation

In some embodiments where the catalyst is unsupported, the catalyst composition is formed via a process comprising the step of contacting a bismuth salt, and (a predetermined amount of) a vanadium precursor, e.g., a soluble $NH_4VO_3$, to form a wet catalyst precursor. Preferably, the process further comprises the step of drying the wet catalyst precursor to form a dried catalyst composition. The dried catalyst composition comprises the components discussed above. The amounts of the bismuth salt and the vanadium precursor are determined such that the resultant dried catalyst composition has a molar ratio of vanadium to bismuth as described herein.

In one embodiment, the process may further comprise the step of mixing the vanadium precursor with a reductant solution to form the vanadium precursor solution. In one embodiment, the reductant solution may comprise an acid, silica, water, and/or a glycol. In one embodiment the acid may be an organic acid that may be oxidized by vanadium, e.g., $V^{5+}$. In an embodiment, the acid may be selected from the group consisting of citric acid, oxalic acid, steric acid, maleic acid, lactic acid, tartaric acid, glycol acid, pyruvic acid, polyacrylicic acid and mixtures thereof. In one embodiment, the acid utilized in the reductant solution does not comprise acids that are not oxidized by vanadium, e.g., $V^{5+}$, e.g., formic acid, acetic acid, succinic acid, and mixtures thereof. In an embodiment, the glycol may be selected from the group consisting of propylene glycol, ethylene glycol, diethylene glycol, triethylene glycol, and other polyols. Preferably, the reductant solution comprises an organic acid, e.g., citric acid and/or oxalic acid, colloidal silica, deionized water, and ethylene glycol. In other embodiments, the reductant solution may also comprise ketones, aldehydes, alcohols, and phenols.

In one embodiment, the formation of the wet catalyst precursor also includes the addition of a binder. Thus, the contacting step may comprise contacting the binder, e.g., a binder solution, with the bismuth salt, and/or the vanadium precursor solution to form the wet catalyst precursor. In one embodiment, the binder may be selected from the group consisting of cellulose, methyl cellulose, carboxylmethyl cellulose, cellulose acetate, cellulose-derived materials, such as starch, and combinations of two or more of the foregoing polysaccharides. In one embodiment, oxides, e.g., silica, may be utilized as a binder. In one embodiment, the catalyst composition comprises at least 3 wt % of the binder, e.g., at least 5 wt % or at least 10 wt %. In one embodiment, an acid, e.g., phosphoric acid, may be added to the wet catalyst composition.

Advantageously, in one embodiment of the present invention, bismuth precursor is added to the wet catalyst mixture prior to phosphorylation, i.e., addition of phosphoric acid solution. In this manner, the bismuth can be incorporated into the metal phosphate matrix of the active phase of the catalyst.

The process, in one embodiment, may further comprise calcining the dried catalyst, which, preferably, is conducted in accordance with a temperature profile. As one example, the temperature profile comprises an increasing stair step temperature profile comprising a plurality of increasing hold temperatures. The temperature increases at a rate from 1° C. to 10° C. per minute between the hold temperatures. Preferably, the hold temperatures comprise a first, second, third, and fourth hold temperature. The first hold temperature may range from 150° C. and 300° C., e.g., from 175° C. and 275° C., preferably being about 160° C. The second hold temperature may range from 250° C. and 500° C., e.g., from 300° C. and 400° C., preferably being about 250° C. The third hold temperature may range from 300° C. and 700° C., e.g., from 450° C. and 650° C., preferably being about 300° C. The fourth hold temperature may range from 400° C. and 700° C., e.g., from 450° C. and 650° C., preferably being about 450° C. Of course, other temperature profiles may be suitable. The calcination of the mixture may be done in an inert atmosphere, air or an oxygen-containing gas at the desired temperatures. Steam, a hydrocarbon or other gases or vapors may be added to the atmosphere during the calcination step or post-calcination to cause desired effects on physical and chemical surface properties as well as textural properties such as increase macroporosity.

In one preferred embodiment, the temperature profile comprises:

i) heating the dried catalyst from room temperature to 160° C. at a rate of 10° C. per minute;

ii) heating the dried catalyst composition at 160° C. for 2 hours;

iii) heating the dried catalyst composition from 160° C. to 250° C. at a rate of 3° C. per minute;

iv) heating the dried catalyst composition at 250° C. for 2 hours;

v) heating the dried catalyst composition from 250° C. to 300° C. at a rate of 3° C. per minute;

vi) heating the dried catalyst composition at 300° C. for 6 hours;

vii) heating the dried catalyst composition from 300° C. to 450° C. at a rate of 3° C. per minute; and viii) heating the dried catalyst composition at 450° C. for 6 hours.

In one embodiment, the catalyst components, e.g., the metal oxides and/or phosphates precursors, may be physically combined with one another to form the catalyst composition. For example the uncalcined dried catalyst components may be ground together and then calcined to form the active catalyst. As another example, the catalyst components may be mixed, milled, and/or kneaded. The catalyst powders formed may then be calcined to form the final dried catalyst composition.

In one embodiment, the phosphorylating agent is added to the mixed metal oxides precursors followed by calcinations.

In one embodiment, the catalyst is prepared under hydrothermal conditions followed by calcinations.

In embodiments where the catalyst is supported, the catalyst compositions are formed through metal impregnation of a support (optionally modified support), although other processes such as chemical grafting or chemical vapor deposition may also be employed.

In one embodiment, the catalysts are made by impregnating the support, with a solution of the metals or salts thereof in a suitable solvent, followed by drying and optional calcination. Solutions of the modifiers or additives may also be impregnated onto the support in a similar manner. The impregnation and drying procedure may be repeated more than once in order to achieve the desired loading of metals, modifiers, and/or other additives. In some cases, there may be competition between the modifier and the metal for active sites on the support. Accordingly, it may be desirable for the modifier to be incorporated before the metal. Multiple impregnation steps with aqueous solutions may reduce the strength of the catalyst particles if the particles are fully dried between impregnation steps. Thus, it is preferable to allow some moisture to be retained in the catalyst between successive impregnations. In one embodiment, when using non-aqueous solutions, the modifier and/or additive are introduced first by one or more impregnations with a suitable non-aqueous solution, e.g., a solution of an alkoxide or acetate of the modifier metal in an alcohol, e.g., ethanol, followed by drying. The metal may then be incorporated by a similar procedure using a suitable solution of a metal compound.

In other embodiments, the modifier is incorporated into the composition by co-gelling or co-precipitating a compound of the modifier element with the silica, or by hydrolysis of a mixture of the modifier element halide with a silicon halide. Methods of preparing mixed oxides of silica and zirconia by sol gel processing are described by Bosman, et al., in *J Catalysis*, Vol. 148, (1994), page 660 and by Monros et al., in *J Materials Science*, Vol. 28, (1993), page 5832. Also, doping of silica spheres with boron during gelation from tetraethyl orthosilicate (TEOS) is described by Jubb and Bowen in *J Material Science*, Vol. 22, (1987), pages 1963-1970. Methods of preparing porous silicas are described in Iler R K, *The Chemistry of Silica*, (Wiley, New York, 1979), and in Brinker C J & Scherer G W *Sol-Gel Science* published by Academic Press (1990).

The catalyst composition, in some embodiments, will be used in a fixed bed reactor for forming the desired product, e.g., acrylic acid or alkyl acrylate. Thus, the catalyst is preferably formed into shaped units, e.g., spheres, granules, pellets, powders, aggregates, or extrudates, typically having maximum and minimum dimensions in the range of 1 to 25 mm, e.g., from 2 to 15 mm. Where an impregnation technique is employed, the support may be shaped prior to impregnation. Alternatively, the composition may be shaped at any suitable stage in the production of the catalyst. The catalyst also may be effective in other forms, e.g. powders or small beads and may be used in these forms. In one embodiment, the catalyst is used in a fluidized bed reactor. In this case, the catalyst may be formed using spray dried or spray thermal decomposition. Preferably, the resultant catalyst has a particle size of greater than 300 microns, e.g., greater than 500 microns. In other cases, the catalyst may be prepared via spray drying to form powders that can be formed into pellets, extrudates, etc.

Production of Acrylic Acid

In other embodiments, the invention is to a process for producing unsaturated acids, e.g., acrylic acids, or esters thereof (alkyl acrylates), by contacting an alkanoic acid with an alkylenating agent, e.g., a methylenating agent, under conditions effective to produce the unsaturated acid and/or acrylate. Preferably, acetic acid is reacted with formaldehyde in the presence of the inventive catalyst composition. The alkanoic acid, or ester of an alkanoic acid, may be of the formula R'—$CH_2$—COOR, where R and R' are each, independently, hydrogen or a saturated or unsaturated alkyl or aryl group. As an example, R and R' may be a lower alkyl group containing for example 1-4 carbon atoms. In one embodiment, an alkanoic acid anhydride may be used as the source of the alkanoic acid. In one embodiment, the reaction is conducted in the presence of an alcohol, preferably the alcohol that corresponds to the desired ester, e.g., methanol. In addition to reactions used in the production of acrylic acid, the inventive catalyst, in other embodiments, may be employed to catalyze other reactions. Examples of these other reactions include, but are not limited to butane oxidation to maleic anhydride, acrolein production from formaldehyde and acetaldehyde, and methacrylic acid production from formaldehyde and propionic acid.

The raw materials, e.g., acetic acid, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Pro-*

*pionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and U.S. Pat. No. 8,143,444, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259 and 4,994,608, all of which are hereby incorporated by reference.

In one optional embodiment, the acetic acid that is utilized in the condensation reaction comprises acetic acid and may also comprise other carboxylic acids, e.g., propionic acid, esters, and anhydrides, as well as acetaldehyde and acetone. In one embodiment, the acetic acid fed to the hydrogenation reaction comprises propionic acid. For example the propionic acid in the acetic acid feed stream may range from 0.001 wt % to 15 wt %, e.g., from 0.125 wt % to 12.5 wt %, from 1.25 wt % to 11.25 wt %, or from 3.75 wt % to 8.75 wt %. Thus, the acetic acid feed stream may be a cruder acetic acid feed stream, e.g., a less-refined acetic acid feed stream.

As used herein, "alkylenating agent" means an aldehyde or precursor to an aldehyde suitable for reacting with the alkanoic acid, e.g., acetic acid, in an aldol condensation reaction to form an unsaturated acid, e.g., acrylic acid, or an alkyl acrylate. In preferred embodiments, the alkylenating agent comprises a methylenating agent such as formaldehyde, which preferably is capable of adding a methylene group (=CH$_2$) to the organic acid. Other alkylenating agents may include, for example, acetaldehyde, propanal, and butanal.

The alkylenating agent, e.g., formaldehyde, may be added from any suitable source. Exemplary sources may include, for example, aqueous formaldehyde solutions, anhydrous formaldehyde derived from a formaldehyde drying procedure, trioxane, diether of methylene glycol, and paraformaldehyde. In a preferred embodiment, the formaldehyde is produced via a formox unit, which reacts methanol and oxygen to yield the formaldehyde.

In other embodiments, the alkylenating agent is a compound that is a source of formaldehyde. Where forms of formaldehyde that are not as freely or weakly complexed are used, the formaldehyde will form in situ in the condensation reactor or in a separate reactor prior to the condensation reactor. Thus for example, trioxane may be decomposed over an inert material or in an empty tube at temperatures over 350° C. or over an acid catalyst at over 100° C. to form the formaldehyde.

In one embodiment, the alkylenating agent corresponds to Formula I.

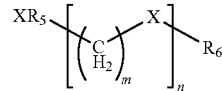

In this formula, $R_5$ and $R_6$ may be independently selected from $C_1$-$C_{12}$ hydrocarbons, preferably, $C_1$-$C_{12}$ alkyl, alkenyl or aryl, or hydrogen. Preferably, $R_5$ and $R_6$ are independently $C_1$-$C_6$ alkyl or hydrogen, with methyl and/or hydrogen being most preferred. X may be either oxygen or sulfur, preferably oxygen; and n is an integer from 1 to 10, preferably 1 to 3. In some embodiments, m is 1 or 2, preferably 1.

In one embodiment, the compound of formula I may be the product of an equilibrium reaction between formaldehyde and methanol in the presence of water. In such a case, the compound of formula I may be a suitable formaldehyde source. In one embodiment, the formaldehyde source includes any equilibrium composition. Examples of formaldehyde sources include but are not restricted to methylal (1,1 dimethoxymethane); polyoxymethylenes —(CH$_2$—O)$_i$— wherein i is from 1 to 100; formalin; and other equilibrium compositions such as a mixture of formaldehyde, methanol, and methyl propionate. In one embodiment, the source of formaldehyde is selected from the group consisting of 1,1 dimethoxymethane; higher formals of formaldehyde and methanol; and CH$_3$—O—(CH$_2$—O)$_i$—CH$_3$ where i is 2.

The alkylenating agent may be used with or without an organic or inorganic solvent.

The term "formalin," refers to a mixture of formaldehyde, methanol, and water. In one embodiment, formalin comprises from 25 wt % to 85 wt % formaldehyde; from 0.01 wt % to 25 wt % methanol; and from 15 wt % to 70 wt % water. In cases where a mixture of formaldehyde, methanol, and methyl propionate is used, the mixture comprises less than 10 wt % water, e.g., less than 5 wt % or less than 1 wt %.

In some embodiments, the condensation reaction may achieve favorable conversion of acetic acid and favorable selectivity and productivity to acrylate product(s). For purposes of the present invention, the term "conversion" refers to the amount of acetic acid in the feed that is converted to a compound other than acetic acid. Conversion is expressed as a mole percentage based on acetic acid in the feed. The overall conversion of acetic acid may be at least 15 mol %, e.g., at least 25 mol %, at least 40 mol %, or at least 50 mol %. In another embodiment, the reaction may be conducted wherein the molar ratio of acetic acid to alkylenating agent is at least 0.50:1, e.g., at least 1:1.

Selectivity is expressed as a mole percent based on converted acetic acid. It should be understood that each compound converted from acetic acid has an independent selectivity and that selectivity is independent from conversion. For example, if 30 mol % of the converted acetic acid is converted to acrylic acid, the acrylic acid selectivity would be 30 mol %. Preferably, the catalyst selectivity to acrylate product, e.g., acrylic acid and methyl acrylate, is at least 30 mol %, e.g., at least 50 mol %, at least 60 mol %, or at least 70 mol %. In some embodiments, the selectivity to acrylic acid is at least 30 mol %, e.g., at least 40 mol %, or at least 50 mol %; and/or the selectivity to methyl acrylate is at least 10 mol %, e.g., at least 15 mol %, or at least 20 mol %.

The term "productivity," as used herein, refers to the grams of a specified product, e.g., acrylate product(s), formed during the condensation based on the liters of catalyst used per hour. A productivity of at least 20 grams of acrylates per liter catalyst per hour, e.g., at least 40 grams of acrylates per liter catalyst per hour or at least 100 grams of acrylates per liter catalyst per hour, is preferred. In terms of ranges, the productivity preferably is from 20 to 800 grams of acrylates per liter catalyst per hour, e.g., from 100 to 600 per liter catalyst per hour or from 300 to 500 per liter catalyst per hour.

As noted above, the inventive catalyst composition provides for high conversions of acetic acid. Advantageously, these high conversions are achieved while maintaining selectivity to the desired acrylate product(s), e.g., acrylic acid and/or methyl acrylate. As a result, acrylate product productivity is improved, as compared to conventional productivity with conventional catalysts.

Preferred embodiments of the inventive process also have low selectivity to undesirable products, such as carbon monoxide and carbon dioxide. The selectivity to these undesirable products preferably is less than 30%, e.g., less than 20% or less than 10%. More preferably, these undesirable products are not detectable. Formation of alkanes, e.g., ethane, may be low, and ideally less than 2%, less than 1%, or less than 0.5% of the acetic acid passed over the catalyst is converted to alkanes, which have little value other than as fuel.

The alkanoic acid or ester thereof and alkylenating agent may be fed independently or after prior mixing to a reactor containing the catalyst. The reactor may be any suitable reactor. Preferably, the reactor is a fixed bed reactor, but other reactors such as a continuous stirred tank reactor or a fluidized bed reactor, may be used.

In some embodiments, the alkanoic acid, e.g., acetic acid, and the alkylenating agent, e.g., formaldehyde, are fed to the reactor at a molar ratio of at least 0.25:1, e.g., at least 0.75:1 or at least 1:1. In terms of ranges the molar ratio of alkanoic acid to alkylenating agent may range from 0.50:1 to 10:1 or from 0.75:1 to 5:1. In some embodiments, the reaction of the alkanoic acid and the alkylenating agent is conducted with a stoichiometric excess of alkanoic acid. In these instances, acrylate selectivity may be improved. As an example the acrylate selectivity may be at least 10% higher than a selectivity achieved when the reaction is conducted with an excess of alkylenating agent, e.g., at least 20% higher or at least 30% higher. In other embodiments, the reaction of the alkanoic acid and the alkylenating agent is conducted with a stoichiometric excess of alkylenating agent.

The condensation reaction may be conducted at a temperature of at least 250° C., e.g., at least 300° C., or at least 350° C. In terms of ranges, the reaction temperature may range from 200° C. to 500° C., e.g., from 300° C. to 400° C., or from 350° C. to 390° C. Reaction pressure is not particularly limited, and the reaction is typically performed near atmospheric pressure. In one embodiment, the reaction may be conducted at a pressure ranging from 0 kPa to 4100 kPa, e.g., from 3 kPa to 345 kPa, or from 6 kPa to 103 kPa.

Water may be present in amounts up to 60 wt %, by weight of the reaction mixture, e.g., up to 50 wt % or up to 40 wt %. Water, however, is preferably reduced due to its negative effect on process rates and separation costs.

In one embodiment, an inert or reactive gas is supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors.

In one embodiment, the unreacted components such as the carboxylic acid and formaldehyde as well as the inert or reactive gases that remain are recycled to the reactor after sufficient separation from the desired product.

When the desired product is an unsaturated ester made by reacting an ester of an alkanoic acid ester with formaldehyde, the alcohol corresponding to the ester may also be fed to the reactor either with or separately to the other components. For example, when methyl acrylate is desired, methanol may be fed to the reactor. The alcohol, amongst other effects, reduces the quantity of acids leaving the reactor. It is not necessary that the alcohol is added at the beginning of the reactor and it may for instance be added in the middle or near the back, in order to effect the conversion of acids such as propionic acid, methacrylic acid to their respective esters without depressing catalyst activity.

EXAMPLES

Example 1

Catalyst compositions were prepared using a bismuth salt $Bi(NO_3)_3$ hydrate and a vanadium precursor, e.g., $NH_4VO_3$. Colloidal silica, deionized water, and ethylene glycol were combined and mixed. An organic acid, e.g. citric acid, was added to the mixture and the mixture was heated to 50° C. A calculated amount of $NH_4VO_3$ was added to the mixture and the resulting solution was heated to 80° C. with stirring. An amount of a bismuth nitrate was added to the heated mixture. A 2 wt % solution of methyl cellulose was added to the bismuth salt/vanadium salt/vanadium precursor solution and stirred at 80 C. A calculated amount of phosphoric acid (85%) was added and the resulting solution was stirred. The final mixture was then evaporated to dryness overnight in a drying oven at 120° C., ground and calcined using the following temperature profile:

i) heating from room temperature to 160° C. at a rate of 10° C. per minute;
ii) heating at 160° C. for 2 hours;
iii) heating from 160° C. to 250° C. at a rate of 3° C. per minute;
iv) heating at 250° C. for 2 hours;

v) heating from 250° C. to 300° C. at a rate of 3° C. per minute;
vi) heating at 300° C. for 6 hours;
vii) heating from 300° C. to 450° C. at a rate of 3° C. per minute; and
viii) heating at 450° C. for 6 hours.

Example 2

Approximately 100 mL of isobutanol was heated to 90° C. in a flask with a mechanical stirrer and condenser. The desired amount of $V_2O_5$ (11.32 g) was slowly added as a powder to the well stirred hot isobutanol. Once the $V_2O_5$ was added, 85% $H_3PO_4$ (8.2 g) was slowly added to the hot mixture with agitation. Once the addition of $H_3PO_4$ was complete, the temperature of the mixture was increased to 100-108° C. and the mixture was stirred at this temperature for about 14 hours.

Bismuth nitrate hydrate (30.2 g) is dissolved in 10% $HNO_3$. $BiPO_4$ was formed and precipitated by the slow addition of diluted $H_3PO_4$ (8.2 g-85% $H_3PO_4$) with constant stirring. The mixture was stirred for 1 hour and then the $BiPO_4$ was collected via filtration or centrifugation. The solid $BiPO_4$ is washed with deionized water three times.

The $BiPO_4$ was added to the $V_2O_5$—$H_3PO_4$-iBuOH mixture and the mixture was stirred and refluxed for one hour. The mixture was allowed to cool and the catalyst in solid form was isolated via filtration or centrifugation. The solid was washed once with EtOH and twice more with deionized water. The solid was dried overnight at 120° C. with flowing air. The dried solid was ground to powder and mixed together and then calcined using the temperature profile of Example 1.

Example 3

Colloidal silica (1.3 g), citric acid (25.7 g), ethylene glycol (18.5 g), deionized water (12 g) were combined and heated to 50° C. with stifling. $NH_4VO_3$ (13.6 g) was added as a fine powder to the citric acid mixture and the resulting solution was heated to 80° C. and stirred for 30 minutes. Bismuth nitrate hydrate (0.9 g) was dissolved in 10% $HNO_3$ solution and slowly added to the vanadyl solution. The mixture was stirred at 80° C. for 30 minutes.

The mixture was cooled and a 2 wt % solution of methyl cellulose (100 g) was added to the mixture and stirred for 30 minutes. Then 85% $H_3PO_4$ solution (15.7 g) was slowly added to the mixture and the resulting solution was stirred for 30 minutes. The final mixture was heated overnight in a drying oven at 120° C. at which time the final mixture underwent thermogellation, which resulted in a porous foam-like material. The resulting foam-like material was ground to mix and calcined using the temperature profile of Example 1.

Table 2 shows surface area, pore volume, and pore size of various catalyst compositions comprising vanadium/bismuth prepared via the methods of Examples 1-3. A bismuth free vanadium catalyst is also provided as comparative example.

TABLE 2

Catalyst Compositions

| Catalyst | Catalyst Formula | Preparation Method | BET Surface Area ($m^2/g$) | BET Ave. Pore Vol. ($cm^3$) | BET Ave. Pore Size (nm) |
|---|---|---|---|---|---|
| 1 | $V_{10}Bi_{0.16}P_{11.7}O_{51}$ | Example 1 2.5% $SiO_2$, 10% methylcellulose | 11 | 0.032 | 12 |
| 2 | $V_{10}Bi_5P_{17.25}O_{70}$ | Example 2 10 mole $V_2O_5$, 5 mole $BiNO_3$ | 10 | 0.024 | 10 |
| 3 | $V_{10}Bi_{0.16}P_{10}O_{46}$ | Example 3 0.16 mole $BiPO_4$, 10 mole $VOPO_4$ | 9 | 0.023 | 10 |
| Comp. A | VPO | Commercial VPO | n/a | n/a | n/a |
| Comp. B | $VP_{1.15}O$ | $NH_4VO_3$, citric acid, 5% $SiO_2$, 10% methyl cellulose | 8.4 | 0.025 | 11.9 |

The effect of Bi doping was studied. The results are presented in Table 2. Catalysts 1 and 3 have a V:Bi ratio of 62.5:1 and Catalyst 2 has a V:Bi ratio of 2:1. Catalyst Comp. A and Catalyst Comp. B are commercially available bismuth free vanadium catalysts. As shown in Table 2, an increase of V:Bi ratio from 2:1 to 63:1 does not appear to significantly affect the surface area, pore volume, and/or pore size of the resultant catalysts.

Example 4

A reaction feed comprising acetic acid, formaldehyde, methanol, water, oxygen, and nitrogen was passed through a fixed bed reactor comprising the catalysts shown in Table 2. The reactions were conducted at a reactor temperature of 375° C. and a GHSV of 2000 $Hr^{-1}$. Acrylic acid and methyl acrylate (collectively, "acrylate product") were produced. The conversions, selectivities, and space time yields are shown in Table 3.

TABLE 3

Acrylate Production

| Catalyst | Runtime (h) | HOAc Conv. (%) | Acrylate Selectivity (%) | Acrylate Yield (%) | Acrylate STY (g/hr/L) |
|---|---|---|---|---|---|
| 1 | 0.6 | 41 | 80 | 33 | 437 |
|  | 0.8 | 42 | 78 | 33 | 435 |
|  | 1.6 | 41 | 81 | 33 | 433 |
|  | 2.4 | 41 | 81 | 33 | 438 |
|  | 2.8 | 41 | 81 | 33 | 430 |
|  | 3.7 | 41 | 81 | 33 | 439 |
|  | 4.2 | 41 | 80 | 33 | 432 |
|  | 5.0 | 41 | 81 | 33 | 435 |

TABLE 3-continued

Acrylate Production

| Catalyst | Runtime (h) | HOAc Conv. (%) | Acrylate Selectivity (%) | Acrylate Yield (%) | Acrylate STY (g/hr/L) |
|---|---|---|---|---|---|
| 2 | 0.8 | 40 | 80 | 32 | 422 |
|   | 2.4 | 40 | 81 | 32 | 426 |
|   | 3.7 | 40 | 80 | 32 | 420 |
|   | 5.0 | 39 | 81 | 32 | 417 |
|   | 6.2 | 40 | 80 | 32 | 416 |
|   | 24.0 | 43 | 79 | 34 | 447 |
|   | 25.2 | 39 | 82 | 32 | 417 |
|   | 26.5 | 39 | 81 | 32 | 415 |
|   | 27.7 | 41 | 80 | 33 | 432 |
| 3 | 1.7 | 38 | 77 | 29 | 381 |
|   | 2.9 | 39 | 77 | 30 | 391 |
|   | 4.0 | 39 | 77 | 30 | 392 |
|   | 5.3 | 39 | 77 | 30 | 393 |
|   | 6.1 | 39 | 78 | 30 | 395 |
|   | 24.9 | 38 | 79 | 30 | 390 |
|   | 26.0 | 38 | 79 | 30 | 395 |
|   | 27.2 | 38 | 79 | 30 | 393 |
| Comp. A | 0.8 | 27 | 85 | 23 | 304 |
|   | 1.7 | 24 | 94 | 22 | 289 |
|   | 2.7 | 23 | 95 | 22 | 280 |
|   | 3.9 | 22 | 97 | 21 | 277 |
| Comp. B | 1.2 | 39 | 77 | 30 | 391 |
|   | 2.3 | 38 | 76 | 29 | 378 |
|   | 3.3 | 37 | 77 | 28 | 369 |
|   | 18.0 | 34 | 73 | 24 | 319 |
|   | 19.3 | 33 | 72 | 24 | 310 |
|   | 20.4 | 31 | 79 | 24 | 315 |
|   | 21.4 | 31 | 78 | 24 | 310 |
|   | 22.5 | 30 | 78 | 24 | 309 |

Acetic acid conversion, acrylate selectivity, acrylate yield, and acrylate space time yield were measured for Catalysts 1-3, Comp. A, and Comp. B at various time points of the reaction. As shown, Catalysts 1-3 maintained steady acetic acid conversion, acrylate selectivity, acrylate yield, and acrylate space time yield over shorter time periods, i.e., Catalysts 1-3 showed little if any catalyst deactivation over shorter time periods, e.g., 5.3 hours or less. In comparison, acetic acid conversion, acrylate yield, and acrylate space time yield for Comp. A and Comp. B decreased after only 3.9 hours and 3.3 hours, respectively. Also, over longer time periods, e.g., for approximately 28 hours, Catalysts 2 and 3 continued to demonstrate maintenance of steady reaction performance, as compared to Comp. B, which deactivated significantly over 22.5 hours. For example, for Comp. B, the acetic acid conversion dropped from 39% to 30%, acrylate yield dropped from 30% to 24%, and the space time yield dropped from 391 g/hr/L to 309 g/hr/L. In addition, the data suggests that even with a small amount of bismuth, the bismuth containing vanadium catalysts provides surprising and unexpected stability over longer time periods. In sum, Catalysts 1-3 surprisingly and unexpectedly demonstrate significant improvements in both short term and long term catalyst deactivation (as measured in acetic acid conversion, acrylate selectivity, acrylate yield, and/or STY) as compared to Comp. A and/or Comp. B.

In addition to the deactivation improvements, Catalysts 1-3, all of which contain bismuth, unexpectedly outperform Comp. A and Comp. B, which are conventional bismuth-free commercially available vanadium catalysts. For example, Catalysts 1-3 demonstrate average acetic acid conversions of 41%, 40%, and 39%, respectively, while Comp. A and Comp. B demonstrate an average acetic acid conversion of only 24% and 34%, respectively. Also, Catalysts 1-3 demonstrate average acrylate STY of 435 g/hr/L, 423 g/hr/L, and 391 g/hr/L, while Comp. A and Comp. B demonstrate average yields of only 288 g/hr/L and 338 g/hr/L. In addition, Catalysts 1-3 demonstrate average acrylate yields of 33%, 32%, and 30%, while Comp. A and Comp. B demonstrate an average yield of only 22% and 26%, respectively. Catalysts 1 and 3 have a V:Bi ratio of 62.5:1. As shown in Table 3, even at a low level, bismuth surprisingly and unexpectedly increases the acetic acid conversion, acrylate selectivity, acrylate yield and/or acrylate space time yield.

Table 4 shows surface area, pore volume, and pore size of an additional catalyst composition comprising vanadium and bismuth prepared via the preparation method of Example 2. Comp. B is also shown as a comparative example.

TABLE 4

Catalyst Compositions

| Catalyst | Catalyst Formula | Preparation Methods | BET Surface Area (m$^2$/g) | BET Ave. Pore Vol. (cm$^3$) | BET Ave. Pore Size (nm) |
|---|---|---|---|---|---|
| 4 | $V_{10}Bi_{0.16}P_{11.7}O_{51}$ | Example 2 10 mole $V_2O_5$, 0.16 mole $BiNO_3$ | 16.3 | 0.042 | 10.3 |
| Comp. B | $VP_{1.15}O$ | $NH_4VO_3$, citric acid, 5% $SiO_2$, 10% methyl cellulose | 8.4 | 0.025 | 11.9 |

Catalyst 4 was prepared as described above. Catalyst Comp. B is a bismuth free vanadium catalyst prepared by reducing ammonium metavanadate with citric acid then adding 5.0 wt % $SiO_2$ and 10% methylcellulose. As shown in Table 4, Catalyst 4 has similar surface area, pore volume, and smaller pore size as the bismuth free vanadium catalyst.

Example 5

A reaction feed comprising acetic acid, formaldehyde, methanol, water, oxygen, and nitrogen was passed through a fixed bed reactor comprising the catalysts shown in Table 4 above. The reactions were conducted at a reactor temperature of 375° C. and a GHSV at 2000 Hr$^{-1}$. Acrylic acid and methyl acrylate (collectively, "acrylates") were produced. The conversions, selectivities, and space time yields are shown in Table 5.

TABLE 5

Acrylate Production

| Catalyst | Runtime (h) | HOAc Conv. (%) | Acrylate Selectivity (%) | Acrylate Yield (%) | Acrylate STY (g/hr/L) |
|---|---|---|---|---|---|
| 4 | 1.8 | 31 | 84 | 26 | 342 |
|  | 2.9 | 31 | 82 | 26 | 335 |
|  | 4.2 | 32 | 81 | 26 | 338 |
|  | 17.6 | 32 | 82 | 26 | 342 |
|  | 18.9 | 33 | 81 | 27 | 347 |
|  | 20.2 | 33 | 81 | 27 | 349 |
|  | 23.4 | 33 | 81 | 27 | 351 |
| Comp. B | 1.2 | 39 | 77 | 30 | 391 |
|  | 2.3 | 38 | 76 | 29 | 378 |
|  | 3.3 | 37 | 77 | 28 | 369 |
|  | 18.0 | 34 | 73 | 24 | 319 |
|  | 19.3 | 33 | 72 | 24 | 310 |
|  | 20.4 | 31 | 79 | 24 | 315 |
|  | 21.4 | 31 | 78 | 24 | 310 |
|  | 22.5 | 30 | 78 | 24 | 309 |

Acetic acid conversion, acrylate selectivity, acrylate yield and acrylate space time yield were measured for Catalyst 4 and Comp. B various time points of the reaction. As shown, Catalyst 4 maintained steady acetic acid conversion, acrylate selectivity, acrylate yield, and acrylate space time yield over both long and short time periods. In comparison, when Comp. B was utilized, the acetic acid conversion, acrylate yield, and acrylate space time yield significantly decreased over the course of 22.5 hours. For example, as discussed above, the acetic acid conversion dropped from 39% to 30% over 22.5 hours, acrylate yield dropped from 30% to 24%, and the space time yield dropped from 391 g/hr/L to 309 g/hr/L.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an acrylate product, the process comprising the step of:
   contacting an alkanoic acid and an alkylenating agent over a catalyst composition under conditions effective to produce the acrylate product, wherein the catalyst comprises a metal phosphate matrix containing vanadium and bismuth.

2. The process of claim 1, wherein the catalyst composition is substantially free of titanium.

3. The process of claim 1, wherein the alkylenating agent comprises a methylenating agent.

4. The process of claim 1, wherein the alkanoic acid comprises acetic acid.

5. The process of claim 1, wherein a molar ratio of alkanoic acid to alkylenating agent is at least 0.50:1.

6. The process of claim 1, wherein an overall alkanoic acid conversion is at least 20 mol %.

7. The process of claim 1, wherein a space time yield of the combination of acrylic acid and acrylates is at least 40 grams/hr/L of catalyst.

8. A process for producing a catalyst composition, the process comprising the steps of:
   (a) contacting the vanadium precursor and the bismuth precursor with a reductant, to form a vanadium/bismuth precursor mixture;
   (b) contacting the vanadium/bismuth precursor and phosphoric acid, to form a metal phosphate matrix containing vanadium and bismuth; and
   (b) calcining the catalyst precursor mixture to form the catalyst composition.

9. The process of claim 8, wherein the catalyst composition is substantially free of titanium.

10. The process of claim 8, wherein the catalyst composition has a molar ratio of vanadium to bismuth ranging from 0.02:1 to 1000:1.

11. The process of claim 8, wherein the vanadium precursor is $NH_4VO_3$.

12. The process of claim 8, wherein the bismuth precursor is bismuth nitrate.

13. A catalyst composition, comprising an active phase comprising:
   vanadium, and
   bismuth, wherein the catalyst composition is suitable for use in an aldol condensation of an alkanoic acid and an alkylenating agent to form an acrylate product.

14. The catalyst composition of claim 13, wherein the acrylate product yield is greater than 30%.

15. The catalyst composition of claim 13, wherein the catalyst composition is substantially free of titanium.

16. The catalyst composition of claim 13, wherein a molar ratio of vanadium to bismuth in the active phase of the catalyst composition ranges from 0.02:1 to 1000:1.

17. The catalyst composition of claim 13, wherein the active phase further comprises phosphorus.

18. The catalyst composition of claim 17, wherein the vanadium, bismuth and the phosphorus form a metal phosphate matrix in the active phase.

19. The catalyst composition of claim 13, wherein the catalyst composition comprises at least 25 wt % vanadium and bismuth, in combination, based on the total weight of the catalyst composition.

20. The catalyst composition of claim 13, further comprises a support selected from the group consisting of silica, alumina, zirconia, titania, aluminosilicates, zeolitic materials, sintered metal supports, ceramic foams, metal forms, honeycombed monoliths, formed metal foils and mixtures thereof.

21. The catalyst composition of claim 13, wherein the catalyst composition further comprises an additive selected from the group consisting of molding assistants, reinforcements, pore-forming or pore modification agents, binders, stearic acid, graphite, starch, methyl cellulose, and glass fibers.

22. The catalyst composition of claim 13, wherein the catalyst corresponds to the formula $$V_a Bi_b P_c O_d,$$

wherein:
   a is 1 to 100,
   b is from 0.1 to 50,
   c is from 1 to 165, and
   d is from 4 to 670.

* * * * *